United States Patent [19]

Dunn

[11] 4,289,123
[45] Sep. 15, 1981

[54] ORTHOPEDIC APPLIANCE

[76] Inventor: Harold K. Dunn, 3848 Cliff Dr., Salt Lake City, Utah 84109

[21] Appl. No.: 135,328

[22] Filed: Mar. 31, 1980

[51] Int. Cl.³ ............................................. A61F 5/04
[52] U.S. Cl. .................................. 128/84 R; 128/92 B
[58] Field of Search ................. 128/84, 69, 75, 92 R, 128/92 A, 92 B, 92 BC, 92 BB, 92 D, 92 BA, 78

[56] References Cited

U.S. PATENT DOCUMENTS

| | | | |
|---|---|---|---|
| 583,455 | 6/1897 | Bush | 128/92 R |
| 2,110,414 | 3/1938 | Bell | 128/84 B |
| 2,774,350 | 12/1956 | Cleveland, Jr. | 128/92 R |
| 3,244,170 | 4/1966 | McElvenny | 128/92 D |
| 3,807,394 | 4/1974 | Attenborough | 128/92 A X |
| 3,862,631 | 1/1975 | Austin | 128/92 B |
| 3,997,138 | 12/1976 | Crock et al. | 128/92 B X |
| 4,033,376 | 1/1977 | McKay | 128/92 R X |
| 4,047,376 | 9/1977 | Hall | 128/92 B X |

FOREIGN PATENT DOCUMENTS 2649042 5/1978 Fed. Rep. of Germany .... 128/92 B

Primary Examiner—Stephen C. Pellegrino
Attorney, Agent, or Firm—M. Reid Russell

[57] ABSTRACT

The present invention in an improved orthopedic appliance is for attachment in supporting engagement to a patient's spine, during an anterior surgical procedure thereof. The installed appliance provides for decompression of the contents of the spinal canal and/or is to obtain sufficient fusion mass to provide long-term spinal stability. The appliance incorporates a pair of contoured rocker arm brackets that are each attached to a separated vertebral portions of healthy vertebra, with a damaged or diseased vertebra therebetween. Spacing adjustment and columnar support between the brackets is provided by a single spacing adjustment rod whose ends are threaded oppositely and are turned into appropriately threaded portions of the brackets. A second slide rod is preferably provided that also extends between the brackets and is arranged to slide freely therein but preferably is arranged to accommodate nuts, or the like, turned thereon against the brackets to provide columnar support thereacross.

7 Claims, 5 Drawing Figures

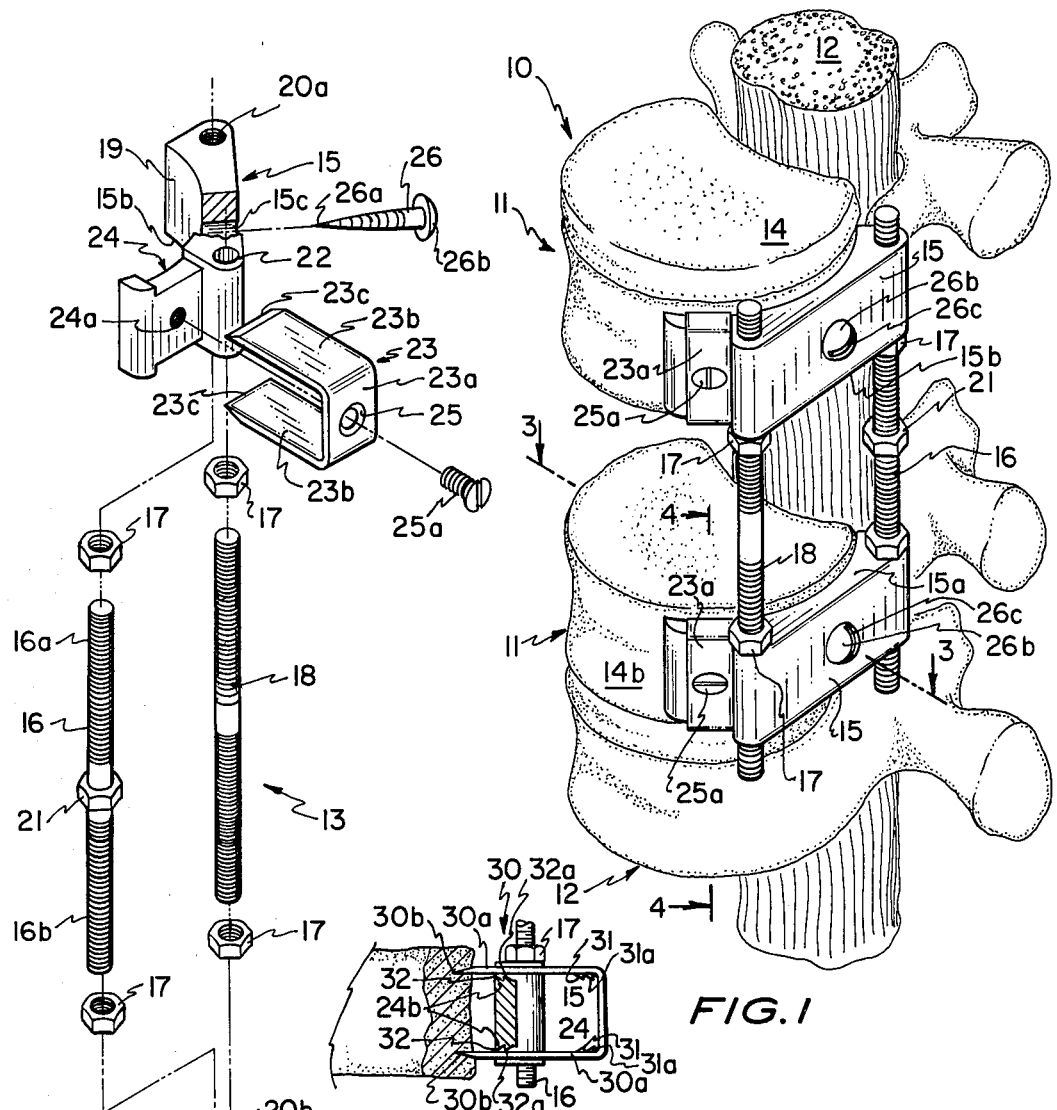

ORTHOPEDIC APPLIANCE

This invention relates to orthopedic appliances for use in certain anterior surgical procedures that involve the human spine.

The present invention in an orthopedic appliance provides a manmade appliance that can be installed into a human skeleton to compensate for a deficiency or defect in the backbone of that human. Similar earlier orthopedic appliances, within the knowledge of the present inventor, have been devices for holding together bone segments or parts to facilitate or make possible the healing processes. Examples of devices for holding together bone parts are shown in early patents by Bush, U.S. Patent No. 583,455, and by Austin, U.S. Pat. No. 3,862,631. These devices are structurally distinct from the present invention.

Devices in other earlier patents by Bell, U.S. Pat. No. 2,110,414; McElvenny, U.S. Pat. No. 3,244,170; and Riniker, U.S. Pat. No. 3,727,610, include some structure that is similar to the present invention, but do not include, as does the present invention, arrangements for permanently supporting the human trunk or a simplified spacing adjustment apparatus or bone attachment arrangements. While a number of fastener devices have been proposed for joining appliances to bone, like those shown in patents by Reeves, et al, U.S. Pat. No. 2,839,815; Forsythe, U.S. Pat. No. 3,866,607; Crock, el al, U.S. Pat. No. 3,997,138; and a Swiss Patent by Muller, No. 373,516, no prior device known to the present inventor has included the staple and screw combination of the present invention.

Contoured devices like the rocker arm brackets of the present invention are not in and of themselves new, and an example of one such contoured device is shown in a German patent by Schollner, Pat. No. 2,283. The Schollner device, however, is not intended for coupling into a human backbone and does not include the particular screw and staple bone coupling arrangement of the present invention.

Further, while a turn-buckle sleeve is shown in a French patent by Carrier, Pat. No. 1,051,847, to connect rods turned in both ends, such arrangement, distinct from the present invention, functions to pull together broken bone segments and is structurally unlike the single rod bracket spacing arrangement of the present invention.

Devices for installation into a human spine in an anterior surgical procedure are not in and of themselves new. An example of such a device is shown in a German patent by Ulrich, Pat. No. 2,649,042, that shows an arrangement of a clip bracket that is attached to a vertebral body protion by a screw that incorporates a head end that is arranged to accommodate a rod installed thereto. The particular clip bracket of the Ulrich device includes a top face for insertion between vertebral body portions for stabilizing the bracket. While the device of the Ulrich patent is intended to assist in the straightening of a curved spine, or the like, it could possibly function like the present invention to provide a support thereto. A device shown in German publications identified as Orthopaedische Praxis, Heft 8, 1975 p.p. 562-560—Avail 128/69, and Arch, Orthop, Unifull—Chir Munich, Vol. 85—1976; Avail—128/69, like the present invention, provides for joining hardware to vertebral body portions of a human spine, but are structurally distinct from the present invention.

The present invention is an improvement over an appliance shown and described in an earlier application for patent by the present inventor, assigned Ser. No. 868,380, filed Jan. 10, 1978, that is now abandoned. The present invention is significantly different therefrom in that it involves a different and improved arrangement for joining rocker arm brackets to vertebral body portions and an improved bracket spacing arrangement.

Therefore, it is a general object of the present invention to provide an appliance for installation in an anterior surgical procedure to a human spine for decompressing the contents of the spinal canal across a damaged or diseased vertebra.

It is an additional object of the present invention to provide an appliance that can be rapidly and easily installed to a person's spine.

Another object of the present invention is to provide an improved orthopedic device for installation to a human spine during an anterior surgical procedure that is easy to install and adjust to permanently provide columnar support across a damaged or diseased vertebra.

In accordance with the above objects, the present invention constitutes an improved orthopedic appliance which is attached, during an anterior surgical procedure, to a patient's spine to take up compressive stresses across a damaged or diseased vertebra. The appliance includes rocker arm brackets that are curved appropriately to conform to the exterior shape of a vertebral body portion and include, as a preferred attachment arrangement for each, a single screw and single staple combination. To attach each bracket to a vertebral body portion, the screw is first turned thereon, and a spacing adjustment rod that spans the brackets is turned to adjust the bracket spacing. Thereafter, the staple is driven into the bone. So arranged, the point of the screw rests approximately between the staple legs providing a rigid and permanent connection of bracket to bone. The brackets preferably have, respectively, threaded lateral holes formed therethrough to be aligned with one another across the damaged or diseased vertebra. The threaded holes are oppositely threaded to accommodate the spacing adjustment rod turned therein. The spacing adjustment rod ends are threaded oppositely such that, by turning the rod, the brackets will be moved towards or away from one another to provide bracket spacing adjustment during a surgical procedure. The unthreaded bracket holes are intended to accommodate a second rod fitted therethrough, which rod functions as a guide rod but is preferably also threaded to accommodate lock nuts thereover. Lock nuts can thereby be turned on both the spacing adjustment rod and guide rod against the opposite inner surfaces of the brackets. So arranged, the improved orthopedic appliance of the present invention will span between an injured or diseased vertebra to decompress the contents of the spinal canal and/or to attain sufficient fusion mass to render long-term stability. Obviously, one or more such improved orthopedic appliances could be installed to a person's spine, depending on the injury or disease thereto.

FIG. 1 is a perspective view of a section of the anterior portion of a person's spine showing a gap between healthy vertebra body portions as representing a missing, damaged or diseased vertebra with the improved orthopedic appliance of the present invention shown attached to healthy vertebral body portions to span that gap;

FIG. 2 shows an exploded perspective view of the improved orthopedic appliance of FIG. 1 removed from the spine;

FIG. 3 is a sectional view taken along the line 3—3 of FIG. 1 showing an arrangement of a screw and staple connectors that join a rocker arm bracket of the improved orthopedic appliance to the healthy vertebral body portion;

FIG. 4 is a sectional view taken along the line 4—4 of FIG. 1 showing the staple connector secured in the vertebral body portions and maintained to the saddle of the rocker arm bracket by a screw; and FIG. 5 is a view like that of FIG. 4 only showing the staple exploded away from the bracket saddle to illustrate a utilization of oppositely facing incline planes for maintaining the staple to the bracket saddle.

FIG. 1 illustrates the attachment of the present invention in an improved orthopedic appliance 13, as shown in FIG. 2, to a human spine that includes individual vertebra 11 and spinal cord 12. As shown therein, a gap is present between vertebra 11 and the present invention in an improved orthopedic appliance 13, hereinafter referred to as appliance, is installed to healthy vertebral body portions 14a and 14b of vertebra 11 to span that gap, which gap represents a missing, damaged or diseased vertebra. The appliance 13 is preferably installed to spine 10 during an anterior surgical procedure where the spine is exposed and the appliance 13 is inserted through the stomach cavity. The appliance 13 consists of a pair of rocker arm brackets 15, each hereinafter referred to as bracket, that are for attachment to healthy vertebral body portions 14a and 14b of individual vertebra 11. Such attachment includes aligning the brackets, such that lateral holes thereacross 20a, 20b, and 22 align, as will be explained in detail later herein, across the gap. Spacing between brackets 15 after connection to vertebral body portions 14a and 14b, is provided by turning of a spacing adjustment rod 16, that has oppositely threaded ends 16a and 16b, and is turned into holes 20a and 20b in brackets 15, that are threaded oppositely to accommodate the rod ends, as shown in FIG. 2. A single nut 21 is preferably centrally secured to rod 16 to be turned by a tool, not shown, to space apart brackets 15 attached to vertebral body portions 14a and 14b. Lock nuts 17 are provided that are turned on the spacing adjustment rod 16 against opposite bracket surfaces 15a and 15b to lock in place the brackets and to transfer compressive stresses thereacross through spacing adjustment rod 16. A slide rod 18 is also provided to fit through aligned lateral holes 22 in brackets 15 to travel freely therein. While lateral holes 22 are preferably not threaded, slide rod 18 can be threaded, as shown in FIGS. 1 and 2, to accommodate lock nuts 17 turned thereon to also engage opposite bracket surfaces 15a and 15b, to provide columnar support between brackets 15. Appropriately turning lock nuts 17 on the spacing adjustment and slide rods 16 and 18 against surfaces 15a and 15b of brackets 15 thereby provides for a transfer of compressive stress across an injured or missing vertebra.

Shown best in FIG. 2, the brackets 15 are preferably contoured at an inner surface 19 to conform to the shape of a vertebral body portion 14a or 14b. Brackets 15 are essentially alike except that the lateral holes 20a and 20b therethrough are threaded oppositely to accommodate the oppositely threaded ends 16a and 16b of spacing adjustment rod 16 turned to space apart appropriately brackets 15, which spacing is then maintained, as described above, by appropriate turning of lock nuts 17 thereon. So arranged, compressive loads are transferred across the missing or damaged vertebra to decompress the contents of the spinal canal and/or to obtain sufficient fusion mass to provide long-term spinal stability.

As shown best in FIG. 2, and in an alternative staple 30 embodiment in FIG. 5, the brackets 15 each preferably accommodate a staple 23 or staple 30 that is fitted over a saddle 24 formed therein proximate to a bracket end. A yoke 23a of a U-shaped staple 23, as shown best in FIG. 2, preferably includes a center hole 25 formed therein. Center hole 25 is intended to align with a threaded hole 24a formed through the bracket saddle 24 to accommodate a conventional screw 25a turned therein to secure the staple 23 to the bracket 25.

FIG. 5 shows another staple 30 embodiment that includes, for providing for permanent attachment to bracket saddle 24, incline planes 31 that project from inner surfaces of staple legs 30a. Incline planes 31, with staple 30 aligned over saddle 24, as shown in FIG. 5, will be elevated as they travel over oppositely facing incline planes 32 that extend outwardly from opposite saddle faces 24b, until incline plane vertical surfaces 31a and 32a align and slide over one another locking the staple 30 to saddle 24.

Each staple 23 or 30 preferably has legs 23b or 30a that have sharpened leading edges 23c and 30b to facilitate its being forced by a tool, not shown, into a vertebral body portion 14a or 14b, as shown in FIGS. 3 and 4. The legs 23b or 30a of each staple 23 or 30 thereby provide broad areas of contact within each vertebral body portion to prohibit canting or pivoting of bracket 15. To further secure each bracket to a vertebral body portion a screw 26, as shown best in FIGS. 2 and 3, is provided that is turned through a hole 15c in bracket 15 into the vertebral body portion, as shown best in FIG. 3. So arranged, the screw end 26a, as shown in FIG. 3, thereby positioned within the vertebral body portion to rest almost between the staple legs to provide, thereby, a rigid coupling of each bracket 15 to a vertebral body portion.

In operation, the brackets 15 are installed to the vertebral body portions 14a and 14b by turning screws 26, as described hereinabove, through hole 15c into the vertebral body portion with a screwdriver, not shown, fitted into a groove 26c in a screw head 26b to apply an appropriate torque thereto. Brackets 15 are thereby attached to each vertebral body portion across a damaged, diseased or missing vertebra and the spacing adjustment rod 16 is then turned, as described, to provide the desired bracket positioning. Of course, before attachment of the brackets 15, the spacing adjustment rod 16 and slide rod 18 are installed in the respective threaded and unthreaded holes 20a, 20b and 22, respectively. With the brackets 15 secured to the vertebral body portions and the spacing adjustment rod 16 turned to move the brackets 15 to appropriately space apart the vertebral body portions, the staples 23 or 30 are then fitted over saddle 24 and are driven, using a tool, not shown, into the vertebral body portion. The staple 30 locks, as described, to the saddle 24, and staple 23 is held thereto by screw 25a, as described. The described screw 26 and staple 23 or 30 provides thereby for three points of connection into each vertebral body portion 14a or 14b, as described to provide for a secure bracket 15 attachment. Thereafter, lock nuts 17 are turned, as shown best in FIG. 1, against the opposite surfaces 15a and 15b of the brackets to provide support across the damaged or missing vertebra.

While a preferred arrangement of brackets 15 with staples 23 and 30 fitted thereto have been shown and described herein, it should be obvious that other arrangements could be provided within the scope of this disclosure. Further, while lock nuts 17 are preferred, it should be obvious that they could be dispensed with, with support to be provided across the brackets by the spacing adjustment rod 16 only. Also, while the permanent attachment of a nut 21 to spacing adjustment rod to provide for turning thereof by a tool, not shown, is preferred, it should be obvious that the spacing adjustment rod itself could be formed with appropriate flattened areas, or the like, to accommodate a tool, or the like, for turning that spacing adjustment rod to provide the described movement apart or together of the brackets 15.

While a preferred embodiment of the present invention in an improved orthopedic appliance has been shown and described herein, it should be understood that the present disclosure is made by way of example only, and that variations are possible without departing from the subject matter coming within the scope of the following claims, which claims I regard as my invention.

What is claimed is:

1. An improved orthopedic appliance consisting of,
a pair of brackets each contoured on one surface to closely fit to a vertebral body portion of a human vertebra, which brackets include oppositely threaded holes formed therethrough that are aligned when the brackets are properly installed to the vertebral body portions;
means for securing each said bracket to a separate vertebral body portion consisting of, a U-shaped staple that includes means for securing it to a saddle portion of each said bracket such that legs of said staple extend outwardly from said bracket contoured surface, and, means, additional to said staple, for connecting each said bracket to said vertebral body portion; and
a spacing adjustment rod having oppositely threaded ends arranged to turn into said oppositely threaded holes in said brackets.

2. An improved orthopedic appliance as recited in claim 1, wherein the means for securing the staple to the bracket saddle include,
a screw fitted through a staple yoke portion and into said bracket saddle.

3. An improved orthopedic appliance as recited in claim 1, wherein the means for securing the staple to the bracket include,
oppositely facing incline planes secured, respectively, to inner faces of legs of said staple and to opposite surfaces of the bracket saddle such that vertical faces of said incline planes will align and slide over one another when said staple is moved over said saddle to lock said staple to said bracket.

4. An improved orthopedic appliance as recited in claim 1, wherein the means, additional to each staple, for securing said bracket to said vertebral body portion consists of,
a screw fitted through an opening through said bracket into said vertebral body portion.

5. An improved orthopedic appliance as recited in claim 1, further including,
slide holes formed through said brackets that align when said brackets are installed to the vertebral body portions; and
a slide rod for installation into said slide holes.

6. An improved orthopedic appliance as recited in claim 5, wherein the slide rod is threaded to accommodate lock nuts turned thereon.

7. An improved orthopedic appliance as recited in claim 1, further including,
lock nuts turned on the space adjustment rod.

* * * * *